United States Patent
Linker et al.

(10) Patent No.: US 7,299,711 B1
(45) Date of Patent: Nov. 27, 2007

(54) ANALYTE SEPARATION UTILIZING TEMPERATURE PROGRAMMED DESORPTION OF A PRECONCENTRATOR MESH

(75) Inventors: Kevin L. Linker, Albuquerque, NM (US); Frank A. Bouchier, Albuquerque, NM (US); Lisa Theisen, Albuquerque, NM (US); Lester H. Arakaki, Edgewood, NM (US)

(73) Assignee: Sandia Corporation, Albuquerque, NM (US)

( * ) Notice: Subject to any disclaimer, the term of this patent is extended or adjusted under 35 U.S.C. 154(b) by 163 days.

(21) Appl. No.: 11/286,015

(22) Filed: Nov. 22, 2005

Related U.S. Application Data

(63) Continuation-in-part of application No. 10/306,939, filed on Nov. 27, 2002, now Pat. No. 6,978,657.

(51) Int. Cl.
G01N 1/22 (2006.01)
(52) U.S. Cl. .................................. 73/863.23
(58) Field of Classification Search .............. 73/863.23
See application file for complete search history.

(56) References Cited

U.S. PATENT DOCUMENTS

| | | | |
|---|---|---|---|
| 4,633,083 A | 12/1986 | Knorr et al. | |
| 4,987,767 A | 1/1991 | Corrigan et al. | |
| 5,014,541 A | 5/1991 | Sides et al. | |
| 5,368,391 A | 11/1994 | Crowe et al. | |
| 5,571,976 A | 11/1996 | Drolet | |
| 5,854,431 A | 12/1998 | Linker et al. | |
| 5,915,268 A | 6/1999 | Linker et al. | |
| 6,085,601 A | 7/2000 | Linker et al. | |
| 6,334,365 B1 | 1/2002 | Linker et al. | |
| 6,345,545 B1 | 2/2002 | Linker et al. | |
| 6,523,393 B1 | 2/2003 | Linker et al. | |
| 6,572,825 B1 | 6/2003 | Linker et al. | |
| 6,604,406 B1 | 8/2003 | Linker et al. | |
| 6,666,907 B1 | 12/2003 | Manginell et al. | |
| 6,787,338 B2 | 9/2004 | Wittwer et al. | |
| 6,792,794 B2 | 9/2004 | Bonne et al. | |
| 6,828,795 B2 | 12/2004 | Krasnobaev et al. | |
| 6,848,325 B2 | 2/2005 | Parmeter et al. | |
| 6,861,646 B2 | 3/2005 | Motchkine et al. | |

(Continued)

OTHER PUBLICATIONS

Franco Basile, A Gas Sample Pre-concentration Device Based on Solid Phase Microextraction (SPME) and Temperature Programmed Desorption (TPD), vol. 31, No. 2, pp. 155-164, 2003.

*Primary Examiner*—Hezron Williams
*Assistant Examiner*—John Fitzgerald
(74) *Attorney, Agent, or Firm*—Robert D. Watson

(57) ABSTRACT

A method and system for controllably releasing contaminants from a contaminated porous metallic mesh by thermally desorbing and releasing a selected subset of contaminants from a contaminated mesh by rapidly raising the mesh to a pre-determined temperature step or plateau that has been chosen beforehand to preferentially desorb a particular chemical specie of interest, but not others. By providing a sufficiently long delay or dwell period in-between heating pulses, and by selecting the optimum plateau temperatures, then different contaminant species can be controllably released in well-defined batches at different times to a chemical detector in gaseous communication with the mesh. For some detectors, such as an Ion Mobility Spectrometer (IMS), separating different species in time before they enter the IMS allows the detector to have an enhanced selectivity.

36 Claims, 12 Drawing Sheets

U.S. PATENT DOCUMENTS

| | | |
|---|---|---|
| 6,870,155 B2 | 3/2005 | Krasnobaev et al. |
| 6,888,128 B2 | 5/2005 | Krasnobaev et al. |
| RE38,797 E * | 9/2005 | Linker et al. ............ 73/863.12 |
| 6,978,657 B1 * | 12/2005 | Baumann et al. .......... 73/28.04 |
| 2003/0155506 A1 | 8/2003 | Motchkine, et al. |
| 2004/0248319 A1 | 12/2004 | Belyakov et al. |
| 2005/0007119 A1 | 1/2005 | Belyakov et al. |
| 2007/0034024 A1 * | 2/2007 | Syage ..................... 73/863.12 |

\* cited by examiner

ANALYTE SEPARATION UTILIZING TEMPERATURE PROGRAMMED DESORPTION OF A PRECONCENTRATOR MESH

CROSS-REFERENCE TO RELATED APPLICATIONS

This application is a Continuation-in-Part application of commonly assigned, application Ser. No. 10/306,939, "Portable Sample Preconcentrator System for Chemical Detection", Baumann et al., filed Nov. 27, 2002 now U.S. Pat. No. 6,978,657 (which received a Notice of Allowability on Sep. 28, 2005), and which is incorporated herein by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

The present invention relates generally to chemical detection systems for detecting trace amounts of chemicals, e.g., explosives or narcotics, on clothes, baggage, vehicles, shipping containers, etc. Detectors used in trace explosives detection systems include ion mobility spectrometers (IMS), mass spectrometers (MS), surface acoustic wave sensors (SAW), electron capture devices (ECD), differential mobility spectrometers (DMS), and chemiluminescence detectors (CLD).

When detecting very small (trace) quantities explosives or narcotics, the sensitivity (i.e., the amount or concentration that can be detected) and the selectivity (i.e., the correct identification of a specific chemical substance from among many other compounds in a sample) of the trace detection system are important, but often competing, factors. With a continuing need to detect even smaller and smaller amounts of explosives or narcotics, the selection of an appropriate detector becomes critical. This includes consideration of the sensitivity, selectivity, cost, size, reliability, duty cycle, and consumables. Since the chemicals of interest have become more complex, greater specificity is needed today to identify individual chemical components.

One approach for increasing detector specificity is to add additional hardware to a detector. For example, a gas chromatograph (GC) column can be added in front of an ion mobility spectrometer (IMS) detector; or an ion trap (IT) can be added in front of a mass spectrometer, to enhance specificity by delaying and, hence, spreading out the arrival times of packets of individual analytes, so that temporal overlap doesn't occur. However, this approach comes at a cost in terms of increased analysis time (typically minutes), added hardware complexity, increased space requirements, greater expenses, and increased maintenance issues.

In general, IMS detectors (and others that use similar operating principles) excel at detecting very small amounts of explosives; including, e.g., low vapor pressure explosives such as TNT, RDX, PETN, and HMX (see FIG. 1). Recently, IMS detectors have been successfully miniaturized as lightweight, hand-portable units (such as disclosed above in co-pending application Ser. No. 10/306,939, which describes a version of the Sandia National Laboratories MicroHound™ sensor platform). However, when a full-size, conventional IMS is reduced in size to a hand-portable unit, its specificity suffers. One reason is because the IMS drift tube has been shortened to about 1-2 inches (as compared to full-size, conventional IMS drift tubes that are 4-6 inches long). With standard full-length drift tubes, multiple chemicals in a complex sample physically separate into unique bunches (i.e., swarms) of individual species as they drift down the long tube. By the time the bunch hits the Faraday plate at the end of the IMS drift tube, the bunches have spread out sufficiently far so that the detector only has to identify a single chemical species. Conversely, when using a short drift tube in a miniature IMS, less physical separation occurs along the drift tube, and, hence, well-defined bunches are less likely to form. Also, with a shorter drift tube, the characteristic drift times are shorter. Consequently, the spectral peaks move closer to each other in drift-time space, and can even overlap, making identification of individual species more difficult; which also increases the rate of false alarms.

Unfortunately, the low vapor pressure explosives currently of interest (e.g., TNT, RDX, PETN, HMX) tend to have characteristic drift times that are inherently similar to one another (regardless of what length drift tube is used). This only magnifies the problem of overlapping spectral peaks when short IMS drift tubes (with short drift times) are used in miniaturized detectors. Also, background contaminants, e.g., cellulose fibers/particles from clothes and fabrics, water vapor, etc. can decompose during the detection phase and interfere with the proper identification of the target chemicals of interest (analytes). Water vapor can also attach to target analytes and affect their drift speeds. Other phenomena, such as thermal decomposition of the analyte molecules when exposed to high desorption temperatures, as well as concentration-dependent chemical reactions (e.g., dimerization of PETN) occurring inside of the IMS reaction chamber, can complicate the analysis and affect the accurate identification of individual species.

Also, there is a specific issue with IMS detectors regarding the depletion of the reactive ion population (RIP) during operation. A small amount of a dopant reactive gas, such as acetone vapor or methylene chloride vapor (depending on the chemistry) is often added to the ionization/reaction chamber of the IMS in order to improve the detector's sensitivity and overall performance, by enhancing the creation of negatively-charged analyte ions (when the detector is operated in the negative-ion mode). As the reactive ions charge-exchange with the analyte molecules, the population of reactive ions is depleted, and the population of analyte ions increases. However, if the reactive ion population drops too low, then the sensitivity of the detector drops dramatically and remains there until the reactive ion population recovers sufficiently. This situation (i.e., excessive depletion) can occur, e.g., when the ionization/reaction chamber is overloaded by an excessively large number of incoming analyte gas molecules (or, for that matter, when overloaded with other background gases or other gases not of interest).

The problem of excessive reactive ion depletion can be addressed, for example, by not presenting the detector with an excessively high concentration of analyte molecules. However, IMS detectors are concentration-dependent devices, meaning that the greater the concentration of incoming analyte gas, the greater the signal to noise (S/N) ratio is. So, these two conflicting requirements (i.e., low analyte concentration to keep reactive ion population high versus high analyte concentration to get a high signal) require careful optimization of the system's design and performance characteristics.

Two different methods are commonly used to collect samples of unknown chemicals, depending on if they are particles or vapors. Small particles are typically collected by swiping a small piece of cotton cloth or flexible metallic mesh across a contaminated surface. Vapors (as well as particles) are typically collected and pre-concentrated by flowing (i.e., moving, vacuuming) contaminated air through a porous metallic filter mesh (such as a stainless steel mesh, felt, or screen). Low vapor pressure explosive molecules are "sticky", meaning that they easily adsorb onto the wires of a metallic mesh. On the other hand, high vapor pressure explosives (see FIG. 1) typically pass through the preconcentrator screen without sticking, which makes them more difficult to collect and pre-concentrate. During collection, concentrated puffs of air can be directed towards a surface to dislodge particles lying on the surface or stuck in clothing, fabrics, etc., which can then be sucked into the preconcentrator module.

Next, in some devices, the contaminated mesh is removed from the preconcentrator module and then placed in a thermal desorption chamber located close to (or, as part of) the detector. Alternatively, the mesh can be heated inside of a combined collection/preconcentrator module without removing the mesh. In either case, we define "desorption chamber" as the location where the contaminated mesh is heated to thermally desorb the collected contaminants. In the desorption chamber, the metallic mesh is heated to about 180 C to 220 C to vaporize and desorb the contaminants. Depending on how fast the mesh is heated up, the contaminants may be released quickly or slowly. Conventionally, the mesh is rapidly heated (i.e., flash heated) in a single short pulse from room temperature to about 200-210 C over a very short period of time, e.g., 0.2-0.4 seconds). When flash heated, almost all of the collected particles and adsorbed vapors are released at essentially the same time; thereby generating a single, concentrated pulse (i.e., packet, bunch, or group) of analyte gas molecules. While the preconcentrator mesh is being heated, a carrier gas (e.g., clean, dry air, nitrogen, helium, etc.), flows through, or across, the mesh and carries the desorbed contaminants along a short gas transfer tube to the chemical detector (such as a ion mobility spectrometer (IMS) or mass spectrometer (MS)).

The metallic preconcentrator mesh is typically heated by flowing a high-amperage electric current through the stainless-steel mesh wires to generate internal heat by Joule-type electric resistance heating. For example, a 12-volt gel-cell type battery can be used to provide 60-80 amps of current through a stainless steel mesh; which is sufficient to raise the peak mesh temperature to about 200 C in about 0.2-0.4 seconds. Alternatively, the mesh may be heated to about 200 C even more rapidly, e.g., in less than 0.01 seconds with concentrated light from a laser or flash lamp (e.g., Xenon lamp).

As explained above, the flash heating of the preconcentrator mesh generates a much greater concentration of analyte gas than could be collected by continuous air sampling and simultaneous detection. Hence, by flash desorbing a metallic preconcentrator mesh, the signal-to-noise (S/N) ratio of the detector can be increased by a factor of 1000× or more; as compared to continuously sampled systems that don't use a preconcentrator mesh. However, when the preconcentrator mesh is flash heated, essentially all of the different species of unknown explosive compounds are released at the same time. While this results in a high concentration of analyte gas presented to the detector, the near-simultaneous arrival of the contaminants can cause the resulting spectral peaks of the IMS spectrum to bunch up and overlap. This makes it more difficult to separate out and identify individual chemical species (such RDX and PETN, which have similar characteristic ion mobility drift times).

Also, flash desorption may release too much gas all at once and wipe out the population of dopant reactive ions in the IMS. If a second batch of analyte molecules were to be subsequently sent in while the reactive ion population was depleted, the subsequent signal generated could be too small for an IMS to detect and analyze.

Another consideration is to minimize the detection system's duty cycle (i.e., the turnaround time required to collect and analyze a sample), in order to more rapidly process large numbers of people, baggage, cars, etc. This becomes especially important for detectors used airports, border crossings, etc., which require high throughput and low false alarm rates. Hence, the detector analysis time, including the thermal desorption step, should be as short as possible.

Also, when the mesh is flash heated to 200 C in 0.2-0.4 seconds, some undesirable chemistry can happen that may result in a more complicated mobility spectrum due to the presence of additional peaks. This can affect the ability of the IMS detection system to identify individual species. For some explosives (e.g., PETN), decomposition occurs at the higher temperatures (especially when approaching 200 C). These decomposition products create extra spectral peaks that would be more prominent when flash heating the mesh, as compared to slowly heating the mesh over a much longer period of time, e.g., 10 seconds, because the decomposition products wouldn't show until much later.

Additionally, there are some concentration related chemical reactions (e.g., dimerization of PETN) that can occur in the drift region of the IMS, which occur more readily when the mesh is flash heated. When flash heated, all of the PETN is volatilized essentially at once, releasing a single packet at a higher concentration to IMS; hence, the probability of PETN molecule-to-molecule collisions is greater at higher concentrations. Alternatively, when a much slower (e.g., 10 s), stepped-temperature profile is used, each individual packet of PETN molecules being sent into the IMS each time, when the temperature is stepped up, has a lower concentration, and, hence, a lower chance of dimerization due to PETN molecule-to-molecule collisions.

What is needed, then is a way to reduce the problem of too closely-spaced real-time and drift time peaks caused by flash desorption of a preconcentrator mesh (i.e., releasing all of the species at once); without increasing the length of the IMS drift tube; without adding too much additional hardware or cost; and without increasing the duty cycle time too much; while, at the same time, allowing the reactive ion population to recover sufficiently in-between heating pulses; reducing decomposition of target molecules at high mesh temperatures; and reducing dimerization of target molecules at high concentrations inside of the IMS; both of which can create additional spectral peaks that can confuse the analysis and identification of individual target species.

SUMMARY OF THE INVENTION

The present invention relates to a method and system for controllably releasing contaminants from a contaminated porous metallic mesh by thermally desorbing and releasing a selected subset of contaminants from a contaminated mesh by rapidly raising the mesh to a pre-determined temperature step or plateau that has been chosen beforehand to preferentially desorb a particular chemical specie of interest, but not others. By providing a sufficiently long delay or dwell period in-between heating pulses, and by selecting the optimum plateau temperatures, then different contaminant species can be controllably released in well-defined batches at different times to a chemical detector in gaseous communication with the mesh. For some detectors, such as an Ion Mobility Spectrometer (IMS), separating different species in time before they enter the IMS allows the detector to have an enhanced selectivity.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

The term "porous mesh" is broadly defined to include other forms of porous structures, in addition to a mesh structure, including a metallic filter, a felt or felt-like mat of finely-drawn wires, a woven screen of metal wires, a porous foamed metal structure, a microporous metallic filter with microholes, and a felt-like mat of sintered metal wires. The term "controllably releasing" means thermally desorbing and releasing a selected subset of contaminants from a contaminated mesh by rapidly raising the mesh to a predetermined temperature step or plateau that has been chosen beforehand to preferentially desorb a particular chemical specie of interest, but not others. For example, PETN preferentially desorbs from a stainless steel mesh at lower temperatures, around 50-100 C, while RDX preferentially desorbs at higher temperatures, around 150-200 C By providing a sufficiently long delay or dwell period in-between heating pulses, and by selecting the optimum plateau temperatures, then different contaminant species can be controllably released in well-defined batches at different times to a chemical detector in gaseous communication with the mesh. For some detectors, such as an IMS, separating different species in time before they enter the IMS allows the detector to have an enhanced selectivity.

Figure 1:
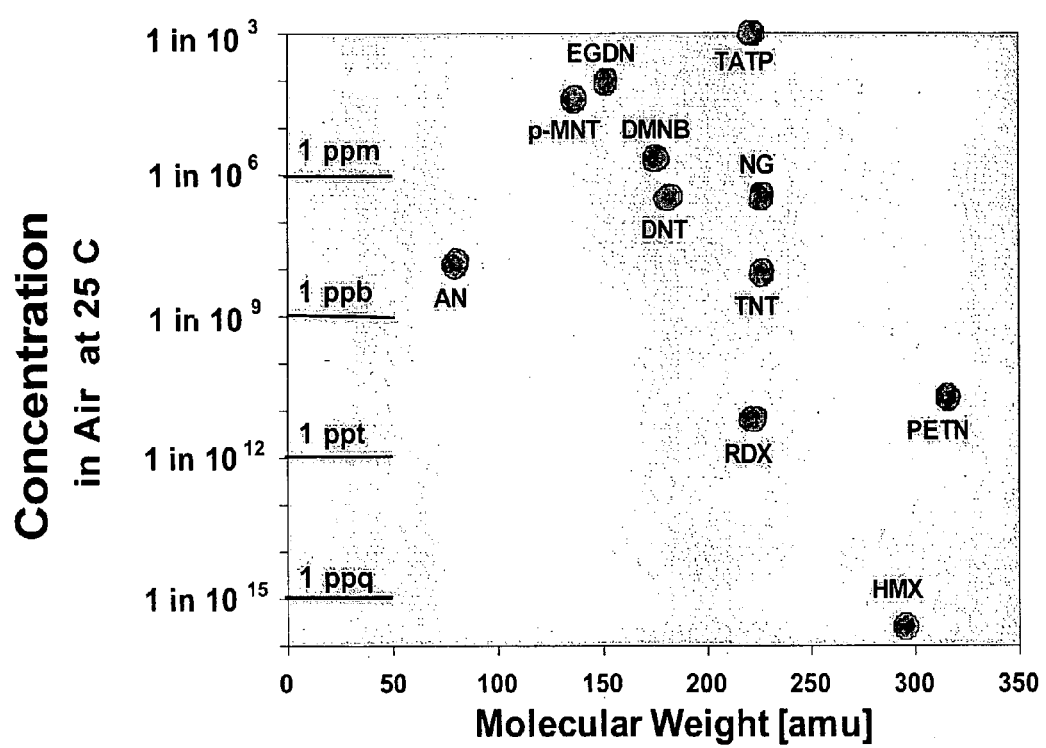
FIG. 1 shows a vapor pressure chart that plots on the y-axis the saturated concentration in air at 25 C for commonly used explosive compounds, as a function of the compound's molecular weight in amu along the chart's x-axis.

FIG. 1 shows a vapor pressure chart that plots on the y-axis the saturated equilibrium concentration in air at 25 C for commonly used explosive compounds, compared to the compound's molecular weight in amu along the chart's x-axis.

Figure 2:
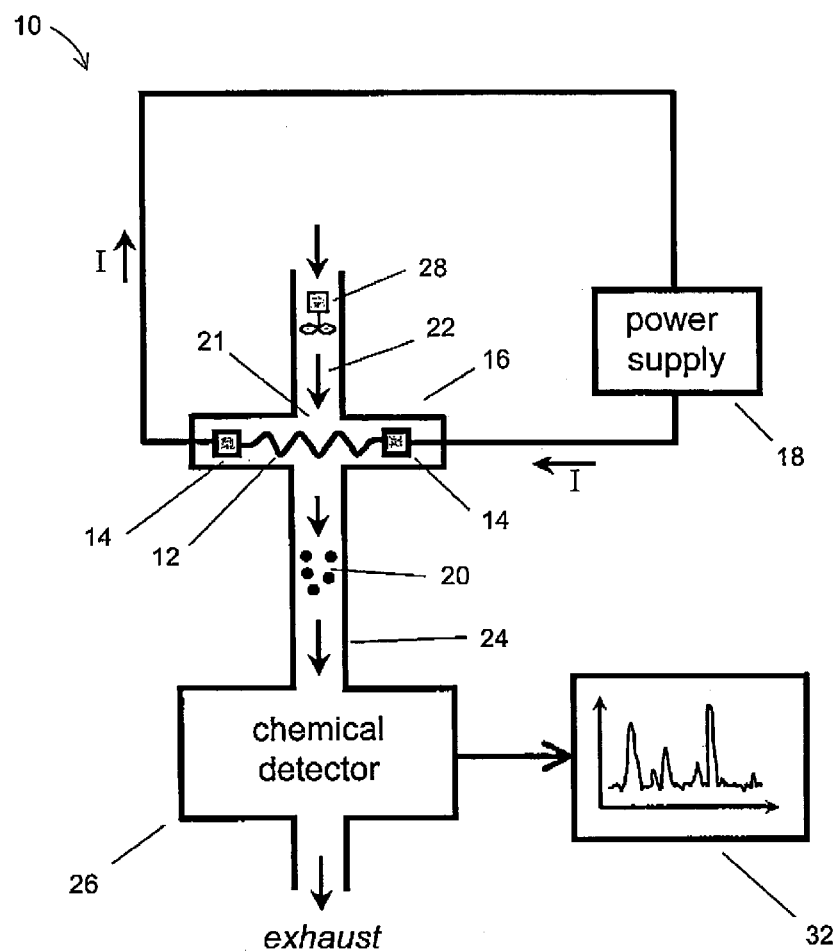
FIG. 2 shows a schematic block diagram of an embodiment of a chemical detection system according to the present invention.

FIG. 2 shows a schematic block diagram of an embodiment of a chemical detection system according to the present invention. Chemical detection system 10 comprises a porous (i.e., pervious) metallic preconcentrator mesh 12 (also referred to as a substrate or sample) held in a mesh holder 14. Mesh holder 14 comprises a structural frame (not shown) that securely holds mesh 12; and includes a pair of spaced-apart electrical contacts (not shown) that make good electrical contact on opposite edges of mesh 12, for driving electrical current from one edge to the other. Alternatively, mesh holder 14 can comprise a pair of electrically-insulated, opposed panels pivotally connected to each other along one edge by a hinge, with panel latching means for clamping and tightly holding the porous metallic substrate (i.e., mesh 12) between the panels, the substrate being electrically insulated from the panels; and a pair of spaced electrical contacts mounted on the panels such that when the substrate is clamped and tightly held by the holder, the contacts touch the substrate and make good electrical contact. A more detailed description of the mesh holder 14 (also called a substrate holder) can be found in U.S. Pat. No. 6,572,825 to Linker and Hannum, and in commonly assigned U.S. patent application Ser. No. 10/306,939 (which received a Notice of Allowability on Sep. 28, 2005), both of which are incorporated herein by reference.

In FIG. 2, system 10 further comprises a desorption chamber 16 in which the mesh holder 14 holding mesh sample 12 can be inserted or placed into and securely held. Desorption chamber 16 has a pair of electrical contacts (e.g., pins, prongs, etc.) that engage the mating electrical contacts on holder 14. The pair of electrical contacts inside desorption chamber 16 are electrically connected to a power supply 18 (e.g., a 12 V battery) that supplies the voltage necessary to drive an electrical current, I, through the metallic preconcentrator mesh 12 (having a resistance, R), via the electrical contacts in mesh holder 14. The flow of electrical current, I, through mesh 12 directly heats the mesh by Joule-type electrical resistance heating, according to eq. (1):

$$P_{heat} = I^2 R \qquad \text{eq. (1)}$$

In previous types of conventional trace chemical detectors, the sample substrates are made of cotton gauze or cloth; or made of plastic or organic fibers coated with chemically-selective organic or polymeric materials. These substrates cannot be directly electrically resistively heated, since they are not sufficiently conductive. Instead, they have to be heated indirectly by flowing hot air across/through the sample, or by indirect radiant heat generated by, for example, a hot filament wrapped around a quartz tube holding the sample. In the present invention, the use of direct electric resistance heating allows the mesh to be rapidly heated in a very short time frame (e.g., 0.1-0.5 seconds), unlike indirect radiant heating (e.g., from a hot filament wrapped around a quartz tube holding the mesh), which heats the mesh much more slowly (e.g., 5 seconds), which is about 10 times more slowly. If the mesh is heated too slowly, e.g., by indirect radiant heating, then the concentration of thermally desorbed analytes will be too low to be detected. Hence, the use of direct electric resistance heating allows the IMS detector to have a much greater sensitivity.

Desorption chamber 16 comprises an inlet for admitting carrier gas 22, which flows through mesh 12 in a direction perpendicular to the broad plane of the mesh. Carrier gas 22 can be driven by fan 28, or supplied by a pressurized gas bottle, canister or cylinder (not shown). Carrier gas 22 can comprise clean and dry air, nitrogen, helium, or other suitable non-reacting gas.

Preconcentrator mesh 12 is contaminated with one or more unknown target chemicals, in the form of small particles on, or embedded inside of, the mesh; or as gas molecules adsorbed to the mesh's surface; or both. Mesh 12 can comprise a metallic filter, a felt or felt-like mat of finely-drawn wires, a woven screen of metal wires, a porous foamed metal structure, a microporous metallic filter with microholes, etc. Mesh 12 can be made of finely-drawn stainless steel wires sintered into a porous, felt-like mat or felt. The stainless steel mesh can be bare, without any coating or coatings of an organic or polymeric material. Bare stainless steel does not have any particular affinity for any of the target analyte molecules of interest. This feature allows the adsorbed analytes to be easily desorbed and released from the stainless steel mesh. Metals other than stainless steel can be used for mesh 12, which have a suitable electrical resistance, including, but not limited to, Ferralloy, Hastalloy, Inconel alloys, Inconel 601, Inconel 625, Inconel 718, etc. A thin gold coating can be disposed on the mesh's surfaces to provide oxidation resistance and prevent chemical reactions between the explosive compounds and, for example the chromium oxide surface of a stainless steel wire. Mesh 12 can be relatively flexible (i.e., for swiping surfaces), or it can be relatively rigid. It can be pre-formed, for example, with a plurality of folded pleats to provide a larger surface area for adsorbing gases and vapors.

Alternatively, mesh 12 can be coated with an organic or polymeric material that can absorb or adsorb a particular chemical or class of chemicals. Such an organic or polymeric coating may be sufficiently thin so as to not completely clog up or fill up the empty spaces in-between mesh wires, pores, filter spaces, etc. Some examples of suitable organic or polymeric materials include: nano-carbon; carbon nanotubes; a carbon molecular sieve adsorbent resin (e.g., Carboxen 569 manufactured by Supelco, inc., Bellefonte, Pa.); a porous polymer resin based on 2,6-diphenylene-oxide (e.g., Tenax TA manufactured by Supelco, Inc.); cyclodextrin and its related compounds, e.g., beta-cyclodextrin, beta-cyclodextrin hydrate, hydroxypropyl-beta-cyclodextrin, hydroxyethyl-beta-cyclodextrin, methyl-beta-cyclodextrin, cycloheptaamylose, and glucose-beta-cyclodextrin; a quaternary ammonium salt; benzalkonium chloride; benzethonium chloride; cetylpyridinium chloride; myristalkonium chloride; benzyl ($C_{12}$-C16) alkydimethylammonium chloride; cetalkonium chloride; cetyl trimethyl ammonium chloride; dodecyl trimethyl ammonium chloride; stearyl trimethyl ammonium chloride; alkyl dimethyl ammonium salt; cetyl tetra ammonium bromide; cetyl trimethyl ammonium bromide (CTAB); a CTAB sol-gel; cetyl ethyl dimethyl ammonium bromide; tetradecyl trimethyl ammonium bromide; tetrabutyl ammonium bromide; cyanopropyl phenyl methyl silicone, and combinations thereof.

Referring still to FIG. 2, desorption chamber 16 comprises an outlet for carrier gas 22 to carry entrained target contaminants to flow to chemical detector 26 via gas transport tube 24. The target contaminants (i.e., analytes) carried by carrier gas 22 comprise particles or gas molecules (or both) that have been thermally desorbed or otherwise released from contaminated mesh 12 when resistively heated to an elevated temperature by power supply 18. Gas transport tube 24 can be insulated and heated to between 100 and 250 C, to prevent analyte molecules from sticking to its walls.

Chemical detector 26 may comprise one or more of the following types of detectors: ion mobility spectrometer (IMS), mass spectrometer (MS), surface acoustic wave sensor (SAW), electron capture device (ECD), differential mobility spectrometer (DMS), chemiluminescence detectors (CLD), gas chromatograph (GC), and thermo redox detector; and miniaturized versions of these, including MEMS versions of these. In some embodiments, a pair of different types of detectors may be combined, e.g., the target analytes exhausted from an IMS can then be introduced into a downstream MS for performing additional analysis and detection. Alternatively, a Gas Chromatograph column may be placed in front to the IMS to slow down and provide some separation between different chemicals. The output 32 of detector 26 may comprise spectrums of various parameters measured by the detector; for example, ion mobility spectral plots of Signal Intensity versus Drift Time (ms), as a function of exposure-time (i.e., clock-time) for an IMS. The signal intensity, drift time, and clock time can be displayed as a 3-D plot called a "plasmagram". Alternatively, the output of detector 26 can be used to provide a simple alert if a certain explosive or narcotic has been detected at all.

Since an IMS detector operates at essentially ambient pressure, it doesn't require a vacuum pump (unlike a mass spectrometer). Not having a vacuum pump frees the detector to be miniaturized into a portable, hand-held platform, such as Sandia's MicroHound II™ platform.

Conventionally, the preconcentrator mesh 12 is flash heated, e.g., to 200 C in 0.2-0.5 seconds, by direct electric resistance heating with a high amperage current (60-80 Amps) generated by effectively shorting out a 12-V lead acid battery across its terminals (by being directly connected to the mesh). When flash heated, essentially all of the different species of target analytes are thermally desorbed and released at the same time, where they travel down the gas transport tube 24 in a single, concentrated bunch (e.g., packet, batch, grouping) of analyte gas molecules 20.

The optimal (i.e., peak) temperature at which a specific target chemical evolves and desorbs from the substrate depends on the enthalpy of adsorption (i.e., the strength of binding to the surface), which is typically different for each individual chemical compound, gas molecule, etc. The surface's condition (clean, dirty, smooth, rough, oxidized, etc.) also affects the desorption behavior. For a given surface concentration and coverage of a particular adsorbed chemical, ramping up the substrate's temperature will cause the adsorbed species to eventually have enough energy to overcome the surface binding forces and escape, thereby raising the pressure of that species in a closed chamber. As the temperature rises still further, the amount of the species left the surface decreases, causing the pressure to eventually drop. This results in a peak in the pressure-vs-time plot when the substrate's temperature increases at a constant rate (i.e., a temperature ramp).

As described previously, this "uncontrolled" release of the contaminants in a single bunch due to flash heating causes a variety of problems. Accordingly, in the present invention, we have replaced the conventional single-step flash heating with a multiple-step temperature/heating profile, which alleviates many of these problems and enhances the detector's selectivity without requiring substantial changes to the detector's hardware.

Figure 3A:
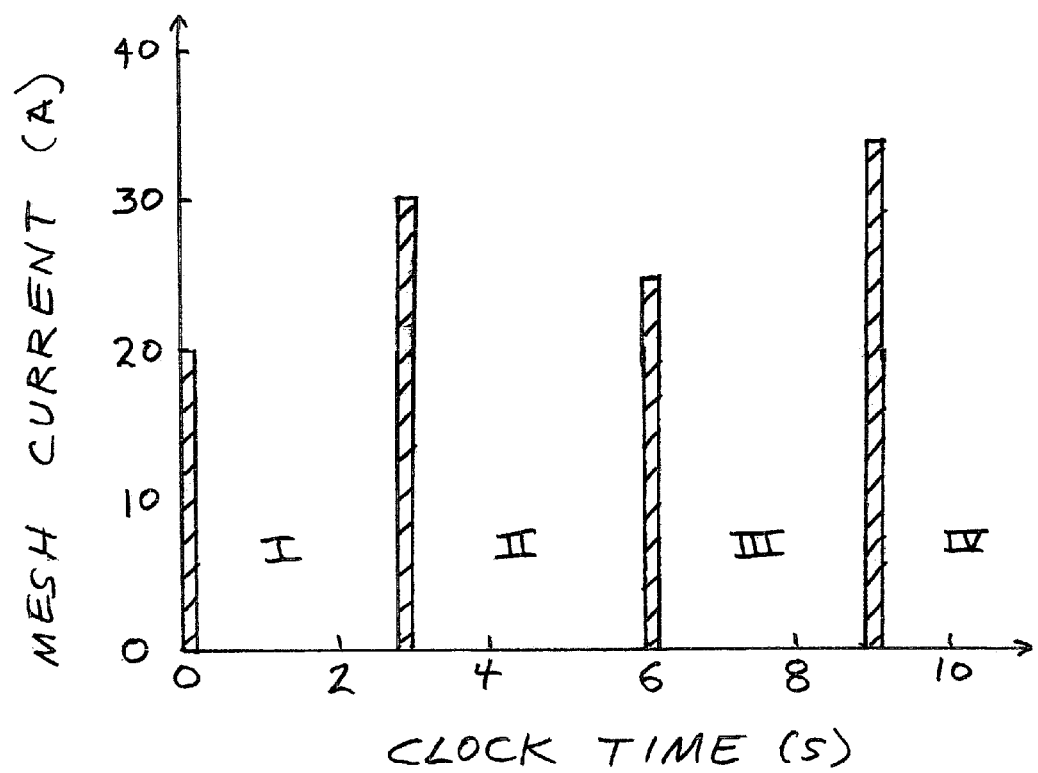
FIG. 3A shows a plot of mesh current (amps) versus clock time (s) for an example of a 4-step heating profile.

FIG. 3A shows a plot of mesh current (amps) versus clock time (s) for an example of a 4-step heating profile. In this example, the electric current (e.g, 20 Amps) is applied to the mesh for 0.3 seconds in a series of four heating pulses; evenly spaced out in time with a delay time (i.e., dwell time) of 3 seconds in-between each heating pulses. During each heating pulse, the temperature rises rapidly and reaches a relatively flat plateau temperature during the delay period when the heating power (i.e., mesh current) is turned off (i.e., in-between heating pulses). This four-step heating profile causes the mesh temperature to rise about 50 C in each step, eventually rising to a peak temperature of about 200 C at the beginning of the $4^{th}$ step at 9 seconds into the desorption cycle. The mesh temperature reaches a relatively flat plateau temperature during the delay period.

Figure 3B:
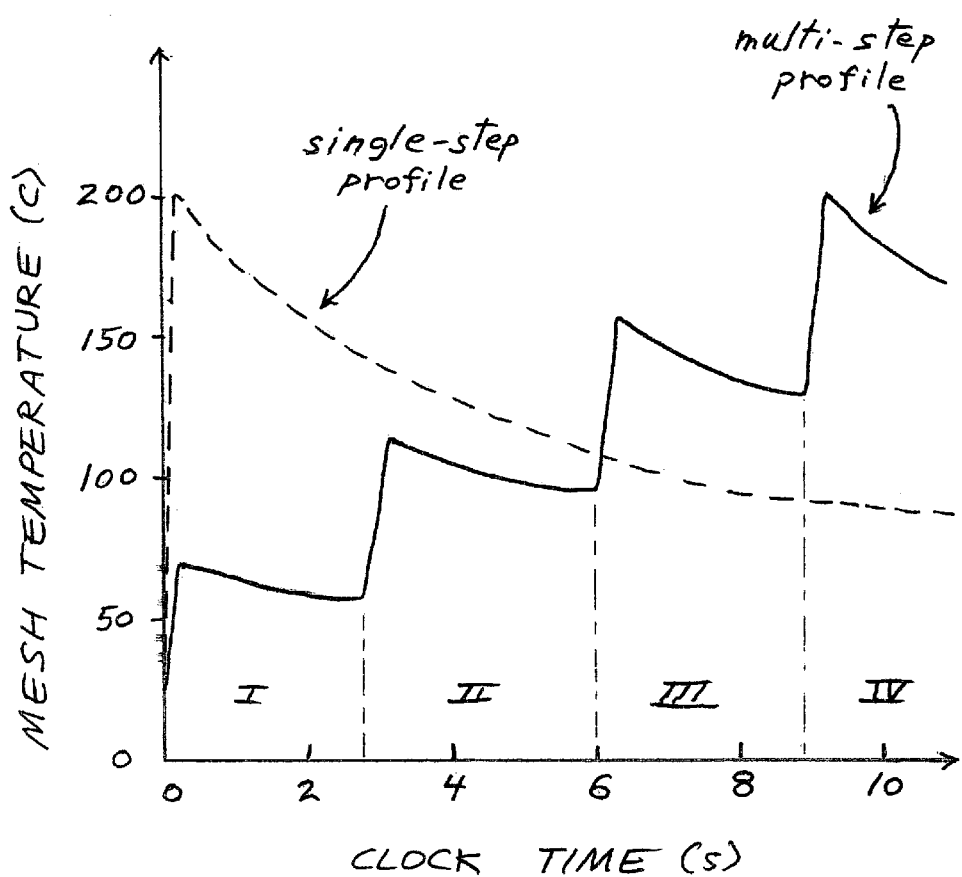
FIG. 3B shows a plot of mesh temperature (C) versus clock time (s) for a single-step profile and an example of a multi-step temperature profile.

FIG. 3B shows a plot of mesh temperature (C) versus clock time (s) for a single-step profile and an example of a multi-step temperature profile. The dashed line illustrates the temperature rise for a conventional single-step, flash-heating profile. Here, a very large electric current (e.g., 80 amps) flows through the mesh for 0.3 seconds, which causes the mesh's temperature to rapidly rise to about 200 C in less than 0.5 seconds, followed by a period of gradual cooling. The solid line illustrates the temperature history of four-step heating profile. Roughly the same amount of total energy (Joules) is deposited in the mesh for both types of temperature profiles illustrated in FIG. 3B; with the four-step profile probably requiring somewhat more energy (i.e., to compensate for the intermediate periods of cooling between temperature steps). However, the multi-step profile allows the user to controllably release individual target chemicals from mesh 12, which is not possible when mesh 12 is flash heated in a single step to 200 C.

An example of a process for executing a thermal desorption cycle can comprise sequentially performing at least two consecutive heating steps, wherein each heating step comprises:

1) applying a heating pulse by resistively heating the mesh for a heating time period by passing an electric current directly through the mesh from one edge of the mesh to an opposite edge of the mesh, thereby generating Joule-type electrical resistance heating directly in the mesh;

2) increasing the temperature of the mesh during the heating pulse and thermally desorbing a batch of contaminant molecules; followed by 3) not heating the mesh for a dwell time period that is at least 2 times longer than the heating time period.

The length of the "heating time period", also called the "heating period" or the "heating pulse" can range, for example from about 0.1-0.5 seconds, but typically would not exceed about 2 seconds in order to prevent accidental mesh overheating. Of course, these specific heating times and dwell times are system dependent, and will need to be adjusted for each different type of chemical detector. The length of the "dwell time period", also called the "delay time", "dwell time", of "plateau period" is typically longer than about 2 seconds. Alternatively, the dwell time period can range, for example, from 2-10 seconds. Alternatively, the dwell time period can be greater than or equal to about 3 seconds. Alternatively, the dwell time period can be at least 2 times longer than the heating time period. The delay time should be greater than or equal to the detector's analysis time, in order to minimize temporal overlapping of multiple species. Also, the delay should be greater than or equal to the recovery time needed to recover a significant fraction (for example, at least 80%) of the original reactive ion population before the next bunch of analytes enters the detector. In our experiments, we have observed that the detector's analysis cycle is completed in less than about 1-2 seconds, and that the RIP recovery time is about 2-3 seconds. In this case, for example, a delay time of at least 3 seconds would satisfy both of these criteria. Of course, a longer delay time would allow for 100% recovery of the RIP reservoir. However, the delay time should be not so long that the mesh cools off too much in-between heating steps; or that the length of the entire desorption cycle becomes excessively long.

A desorption cycle may be sub-divided into any number of steps, according to the present invention. However, it typically ranges from 3-6 steps. If the minimum delay time is 3 seconds or more, then increasing the number of steps beyond 6 would cause the total desorption cycle to be longer than about 20 seconds, which would adversely affect the sample throughput rate. Clearly, there is a tradeoff between having a longer sample analysis time (including the desorption cycle), and having a shorter sample turnaround time for a busy facility. A dwell time of 3-4 seconds appears to be about optimum for using these systems at a busy facility. Having a short sample turnaround time is also desirable when a large number of samples need to be collected, for example, at a suspected terrorist's location.

Optionally, the length of the "heating pulse time" and/or the "dwell time" can vary from one heating step to the next, although typically they would remain the same during a desorption cycle. Note that the specific time at which the peak mesh temperature occurs, during any given heating step, is near the end of the resistance heating pulse, or shortly beyond, since the mesh's wires are very thin with low thermal mass; and because the heat energy is internally generated by resistance heating. For example, for a 0.3 second pulse heating time, the peak mesh temperature would occur at between a few hundred milliseconds seconds after the end of the pulse heating time, e.g., at 0.4-0.5 seconds. The mesh's actual temperature can be measured in a variety of different ways, for example, by a small IR sensor looking at the mesh, or by an attached thermocouple. The multi-step temperature profile can optionally include an initial quick heat to 50-75 C to help get rid of any water, and to help get an initial IR temperature reading. An initial pre-heating step becomes important when the detection system is used in a cold environment.

Table 1 shows an example of a six-step temperature profile that has been optimized for IMS trace detection of the common low vapor pressure explosives. Here, the desorption cycle is sub-divided into 6 heating steps of equal length, with a dwell time of 3 seconds, and a heating period of about 0.3 seconds. As will be described later, the heating period may be automatically lengthened by the system, as needed, to compensate for a lower battery voltage.

TABLE 1

Example of a Six-Step Temperature Profile

| Heating Step No. | Peak Mesh Temperature (C.) |
|---|---|
| 1 | 70-75 |
| 2 | 90-95 |
| 3 | 140-145 |
| 4 | 160-165 |
| 5 | 195-200 |
| 6 | 205-210 |

We have performed experiments that successfully confirm the beneficial aspects of sub-dividing the single-step flash heating into a multi-step heating profile.

Figure 4:
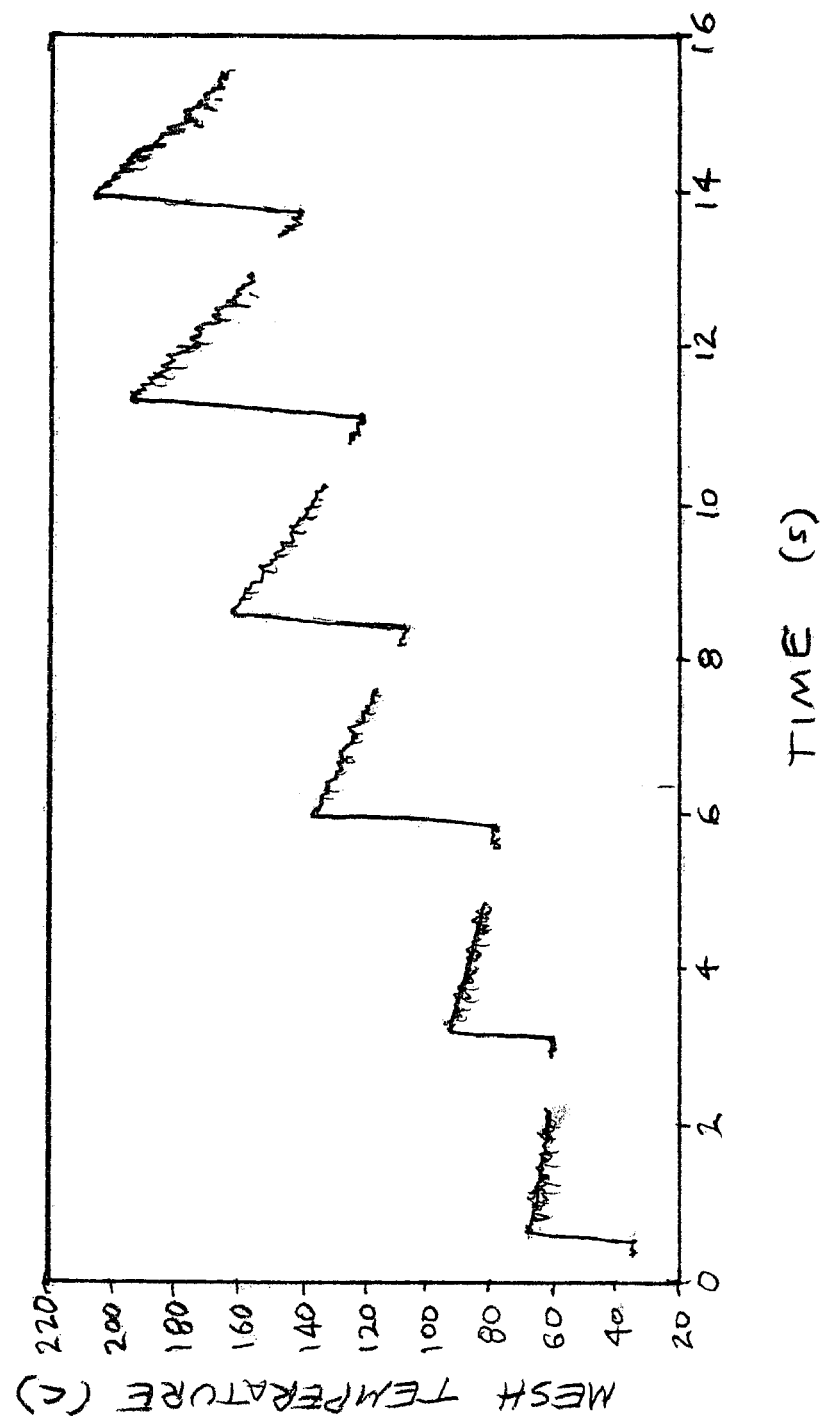
FIG. 4 shows an experimental plot of measured mesh temperatures for a six-step temperature profile.
Figure 5A:
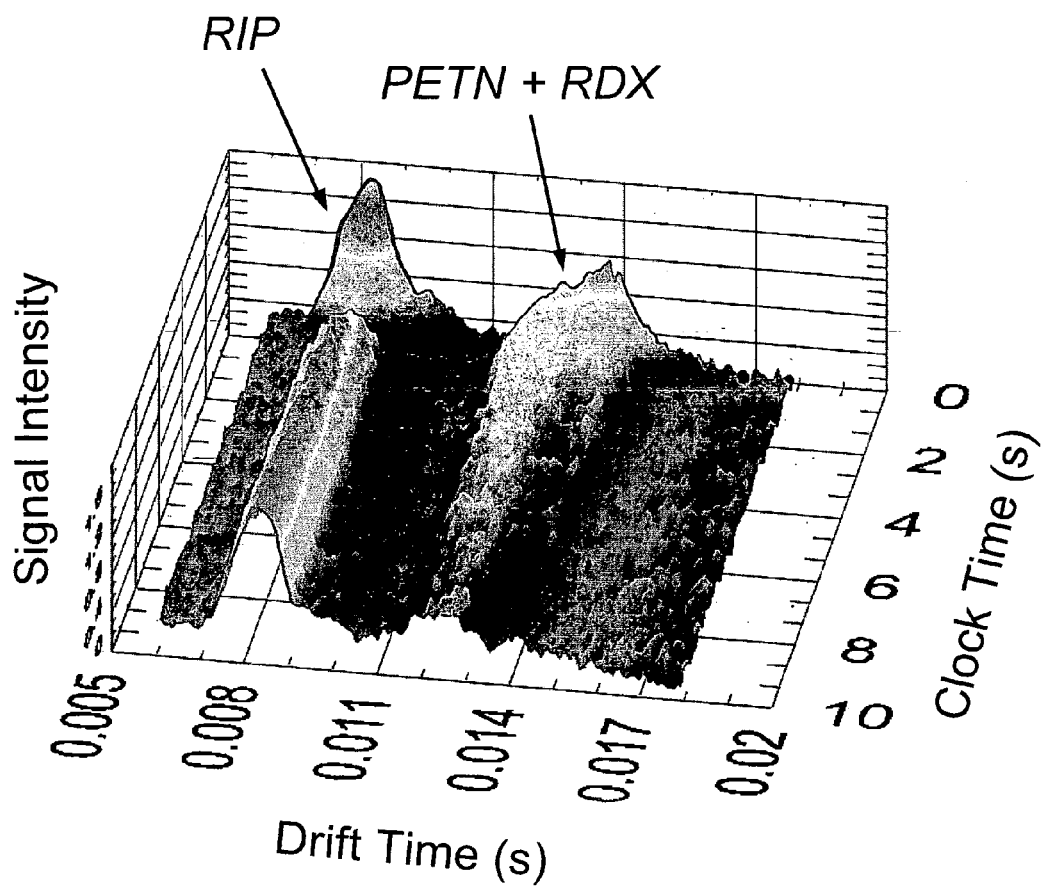
FIG. 5A shows a 3-D "plasmagram" plot of experimental data for IMS detector signal intensity (ab. units) versus clock time (s) and drift time (s) for a sample containing 40 ng of RDX and 40 ng of PETN, when flash-heated to 189 C with a conventional single-step heating pulse lasting about 0.3 seconds.

FIG. 4 shows an experimental plot of measured mesh temperatures for a six-step temperature profile. The mesh temperatures (measured by an IR sensor) corresponding roughly to the "optimum" temperature profile listed in Table 1. In the dwell period in-between heating pulses, the mesh temperature is not exactly a flat plateau, but, rather, decreases somewhat over time due to cooling. The rate at which the mesh cools off during the dwell period depends on various factors, including, e.g., the weight of the mesh, how well the mesh conducts heat to support holder 14, how well the mesh radiates temperature to its surrounding environment, and how well a flowing carrier gas convects heat away from the mesh (which would depend on the gas flow rate and temperature). The primary purpose of incorporating a plateau period, during which the temperature is relatively constant, FIG. 5A shows a 3-D "plasmagram" plot of experimental data for IMS detector signal intensity (ab. units) versus clock time (s) and drift time (s) for a sample containing 40 ng of RDX and 40 ng of PETN, when flash-heated to 189 C with a conventional single-step heating pulse lasting about 0.3 seconds. Methylene chloride was used as the reactive ion species. In the IMS system used in these experiments, the reactive ion population (RIP) has a characteristic drift time of about 8 ms; RDX has a characteristic drift time of about 12 ms, and PETN has a characteristic drift time of about 14 ms. Taking a slice through the plasmagram at a constant 8 ms drift time, one can see that the reactive ion population is quickly depleted during the first second (due to the load of incoming analytes), but then recovers to more than 80% of its original level after about 2-3 seconds. Even though the mesh temperature reaches it's peak in about 0.5 seconds, it takes an additional 0.5-1.0 seconds for the majority of desorbed analyte molecules be processed by the detector. Since nearly all of the RDX and PETN target analytes are desorbed in the first 0.5 seconds or so, their IMS signal intensities reach a peak in about 1-1.5 seconds. Thereafter, the 14 ms (PETN) response rapidly drops off, while the 12 ms (RDX) curve decays more slowly over time. Since both the 12 and 14 ms responses reach their maximum intensities at roughly the same time (e.g., at 1-1.5 seconds), this temporal overlapping makes it difficult for the detector to separate out and correctly identify the individual species of RDX and PETN.

Figure 5B:
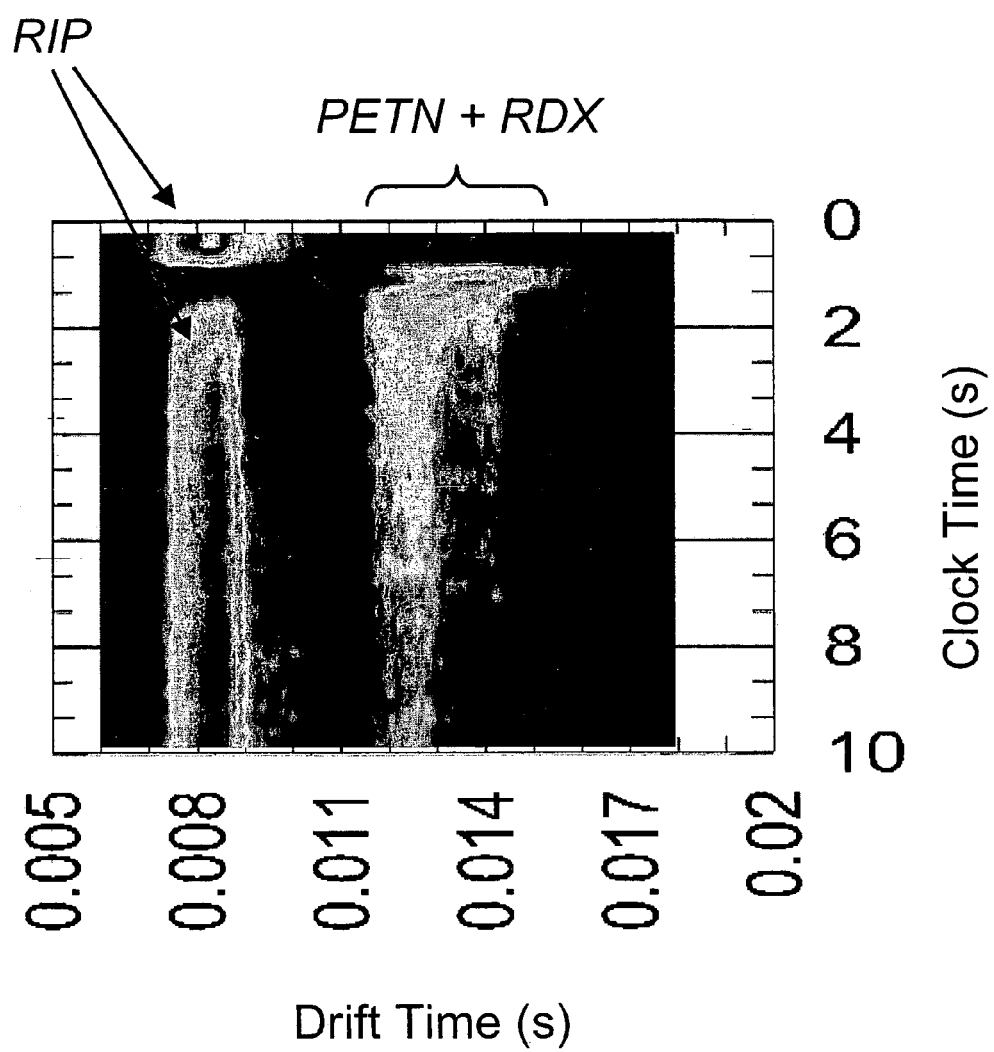
FIG. 5B shows the 2-D, "birds-eye" view of the plasmagram showed in FIG. 5A.

FIG. 5B shows the 2-D, "birds-eye" view of the plasmagram showed in FIG. 5A. At 1 second, the spectral peak is centered around 14 ms drift time and has a wide distribution on both sides. At the longer times, e.g., 3, 6, and 9 seconds, the peak decreases in magnitude and shifts gradually towards 12 ms drift time, while continuing to have a wide distribution. The wide, overlapped spectral distribution is caused by introducing both target species (RDX and PETN) to the detector's ionization chamber at the same time. This temporal overlap makes it difficult to separately identify the individual species of RDX and PETN.

Figure 6A:
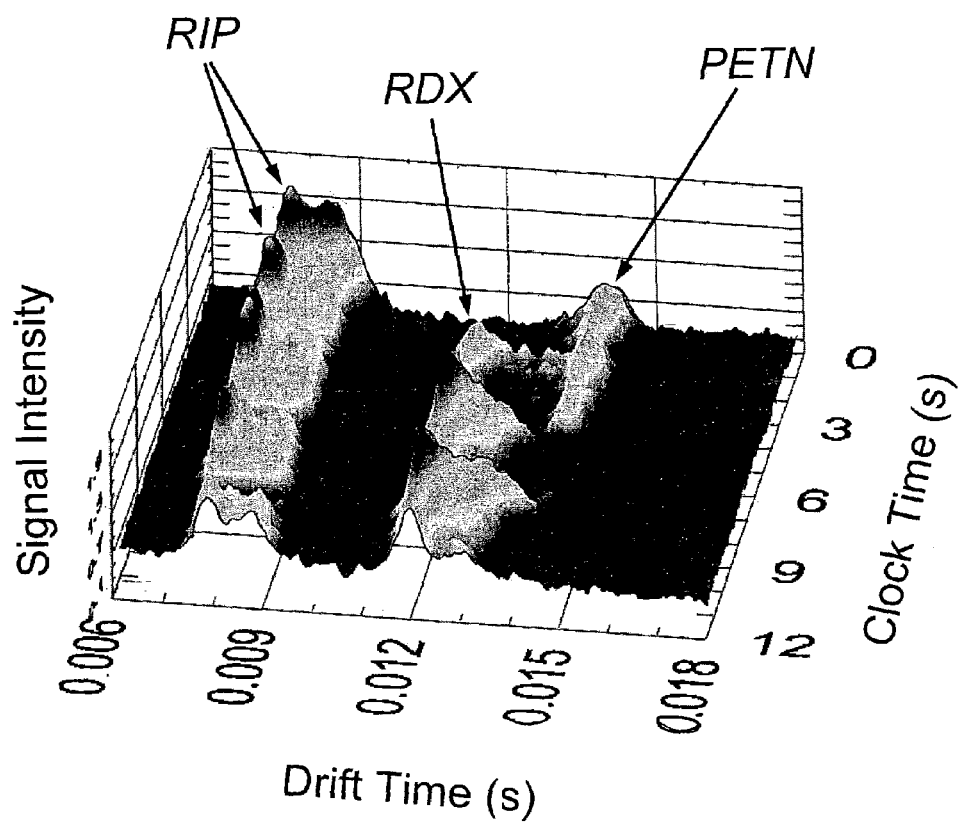
FIG. 6A shows a 3-D "plasmagram" plot of experimental data for IMS detector signal intensity (ab. units) versus clock time (s) and drift time (s) for a sample containing 80 ng of RDX and 80 ng of PETN, when heated to 195 C using a 4-step temperature profile, with a dwell time of about 3 seconds between heating pulses.

FIG. 6A shows a 3-D "plasmagram" plot of experimental data for IMS detector signal intensity (ab. units) versus clock time (s) and drift time (s) for a sample containing 80 ng of RDX and 80 ng of PETN, when heated to 195 C using a 4-step temperature profile, with a dwell time of about 3 seconds between heating pulses. Methylene chloride was used as the reactive ion species, and the test setup is the same as used before with the single-step flash-heated sample in FIGS. 5A, 5B. Here, we see that the reactive ion population is quickly depleted each time the mesh temperature is stepped up, but recovers during the 3 second delay period (note: the temperature history corresponding to this test is schematically illustrated in FIG. 3B, where the peak temperatures are approximately equal to 50, 100, 150, and 200 C; corresponding to each of the four sequential heating pulses).

The IMS detector's response in FIG. 6A is quite different than in FIG. 5A. Using a multi-step temperature profile, the 14 ms drift time response (corresponding to PETN) quickly rises to a maximum level with about 1 second, and remains high until the third pulse starts at 6 seconds, whereupon it drops off quickly. This confirms that the PETN is being controllably released during the first two temperature steps (50, 100 C), but not in the $3^{rd}$ and $4^{th}$ steps (since essentially all of the PETN has been desorbed at the lower temperatures). On the other hand, the 12 ms drift time response (corresponding to RDX), has a relatively low signal intensity during the first two temperature steps, which then rises to its peak values at 6 and 9 seconds, corresponding to the $3^{rd}$ and $4^{th}$ temperature steps (150 and 200 C). In the case of RDX, the mesh temperatures during the $1^{st}$ and $2^{nd}$ steps are too low to overcome the binding energy of RDX to the stainless steel mesh, and the RDX is not desorbed or detected. However, at the higher temperatures in the $3^{rd}$ and $4^{th}$ steps, the RDX is controllably released and readily detected. These results show that by subdividing the temperature history into multiple-steps with relatively-flat plateaus, the two different species of contaminants are each controllably-released to the detector with sufficiently different periods of time (1-6 seconds for PETN, and 6-12 seconds for RDX) that there is minimal temporal overlap between bunches of analytes. This allows the detector to more easily and accurately correctly identify the individual chemicals.

Figure 6B:
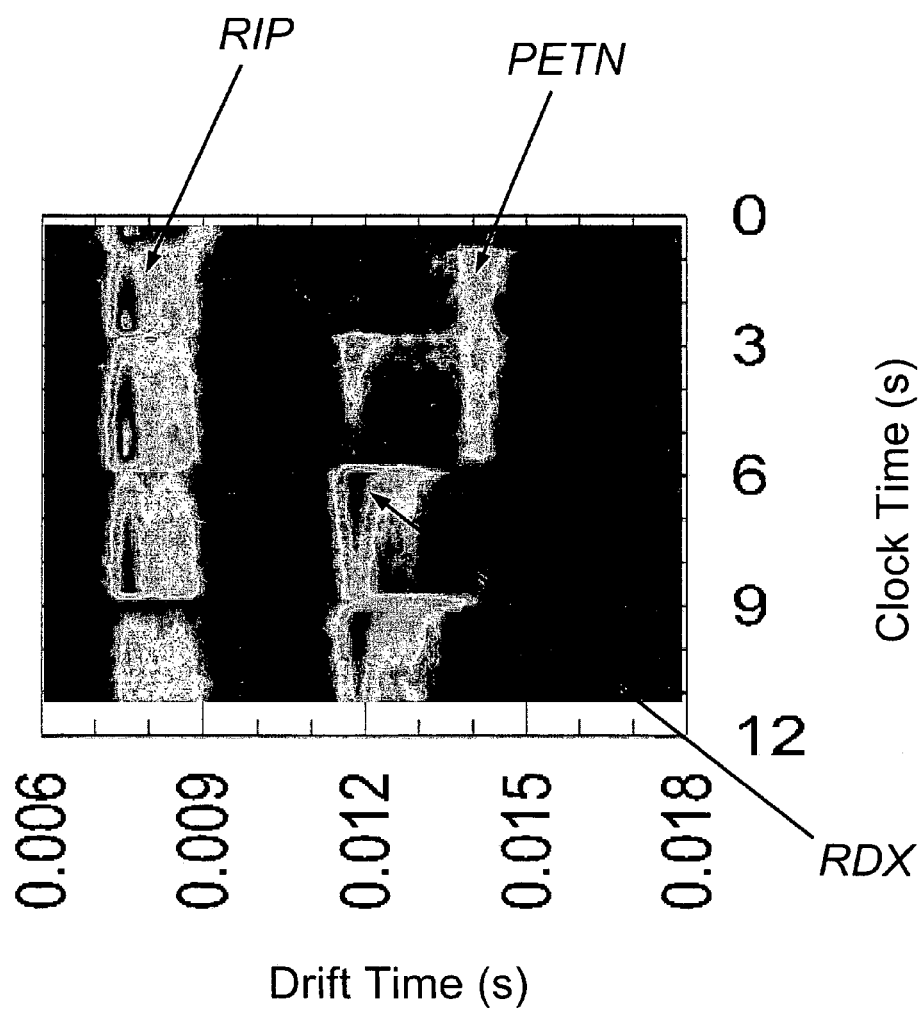
FIG. 6B shows the 2-D, "birds-eye" view of the plasmagram showed in FIG. 6A.

FIG. 6B shows the 2-D, "birds-eye" view of the plasmagram showed in FIG. 6A. At 1 second, the spectral peak is centered at 14 ms drift time and has a narrow distribution on both sides (which corresponds well to the known spectrum of PETN). Later, at 6 seconds, the peak is now centered at 12 ms drift time, and also has a narrow distribution (which corresponds well to the known spectrum of RDX). Due to the time separation caused by the multi-step thermal desorption profile, the two different contaminants were well-separated and correctly identified, despite having relatively similar characteristic drift times (12 ms, 14 ms).

Returning now to the example of a detection system shown in FIG. 2, power supply 18 provides pulses of high electric current (e.g., 20-80 amps) for short periods of time (e.g., 0.3 seconds) to resistively heat mesh 12. Supply 18 may comprise a digitally-programmed power supply, e.g., supplied by AC house current (120 V), wherein the heating profile can be pre-programmed for a multi-step heating current profile. This can be done, for example, by generating a conversion table between the desired plateau temperature for each individual step and the power level (i.e., output current) and pulse length of supply 18 needed to reach that plateau temperature.

Alternatively, power supply 18 may comprise a DC battery 40 connected to a high-current capacity (e.g., 100 amp capacity), relay-controlled switch 42 (e.g., MOSFET switch). A battery-powered system is useful for lightweight, hand-held trace detection systems, such as Sandia's Micro-Hound™. A problem, however, with using a DC battery is the loss of current capacity and battery voltage over time due to aging or damage, which may not be readily predictable. Battery aging, if not corrected for, can cause a gradual drop in the peak mesh temperature over a period of days or weeks (depending on usage), leading to inconsistent results when comparing to previous tests. We have developed a simple analog circuit called the "Integrating Preconcentrator Heat Controller" circuit (IPHC), that can adjust the period of time that the high current flows through the mesh. Typically, the IPHC would increase the heating time for a reduced battery. A detailed description of an IPHC circuit can be found in the commonly-assigned, co-pending application, INTEGRATING PRECONCENTRATOR HEAT CONTROLLER, by Bouchier, Arakaki and Varley, filed Jan. 27, 2006, Ser. No. 11/341,764, which is incorporated herein by reference.

Figure 7:
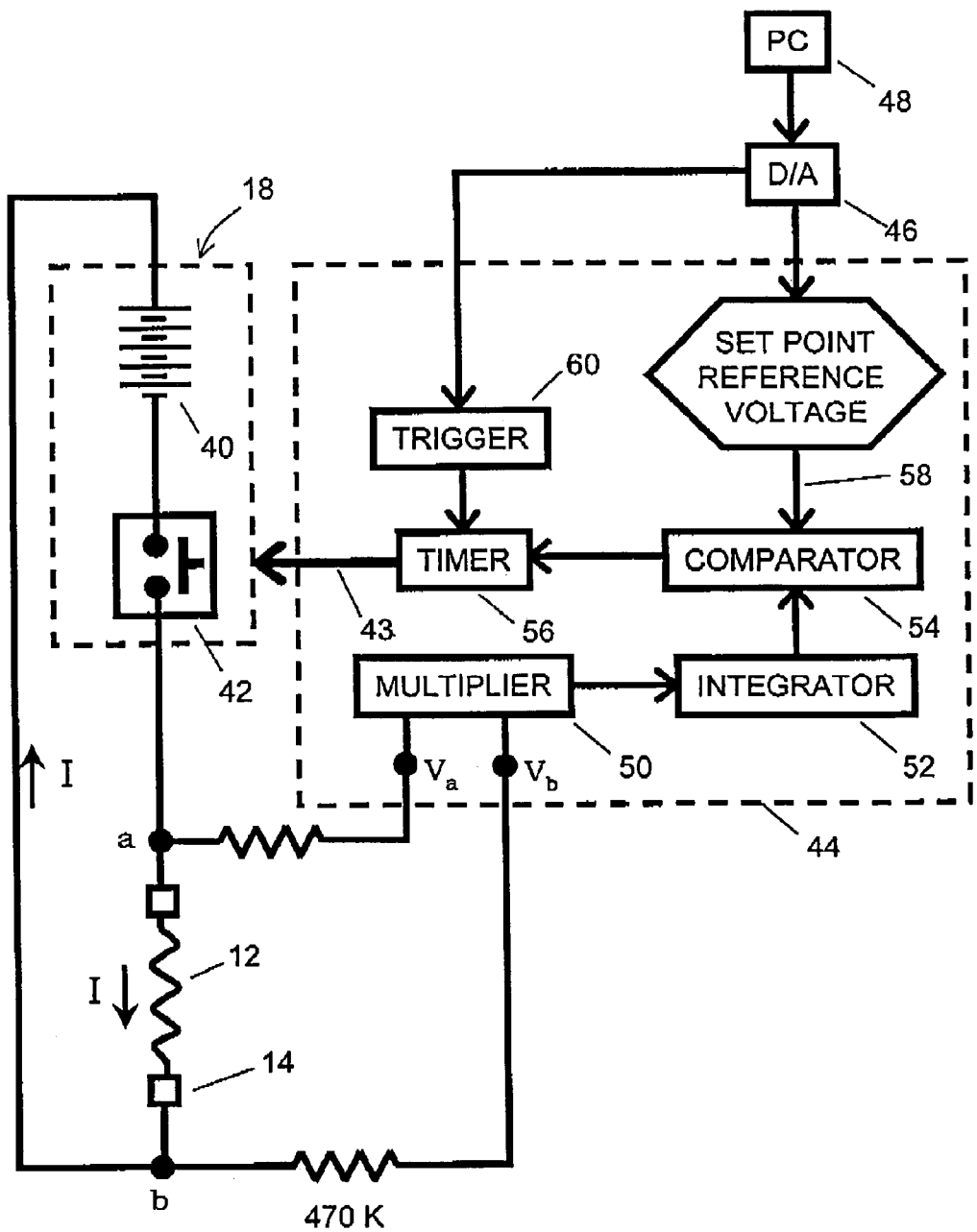
FIG. 7 shows an example of a battery-powered supply 18 combined with an analog IPHC circuit 44 that controls the length of the heating period.
Figure 8A:
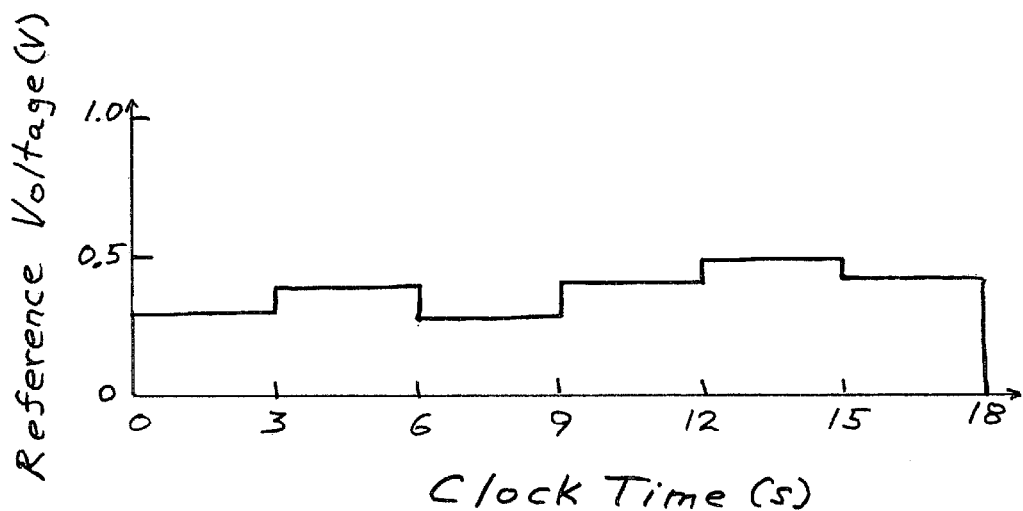
FIGS. 8A-D show examples of profiles of (A) Reference Voltage, (B) Trigger Voltage, (C) Mesh Current, and (D) Mesh Temperature, as a function of clock time for a 6-step desorption cycle and a pleated mesh.
Figure 8B:
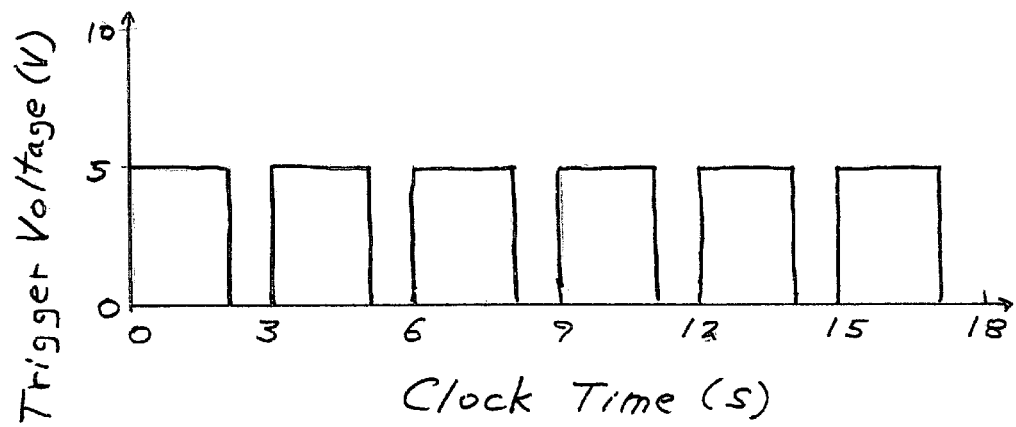
Figure 8C:
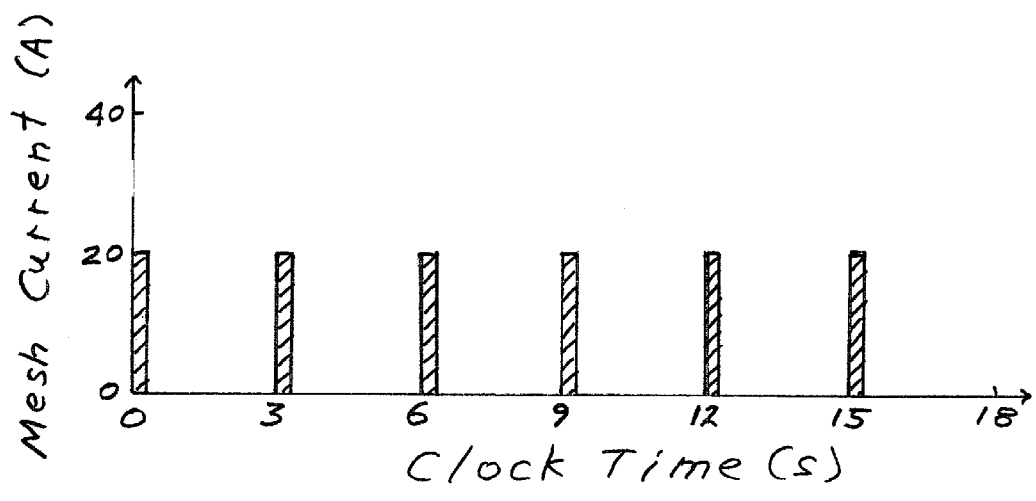
Figure 8D:
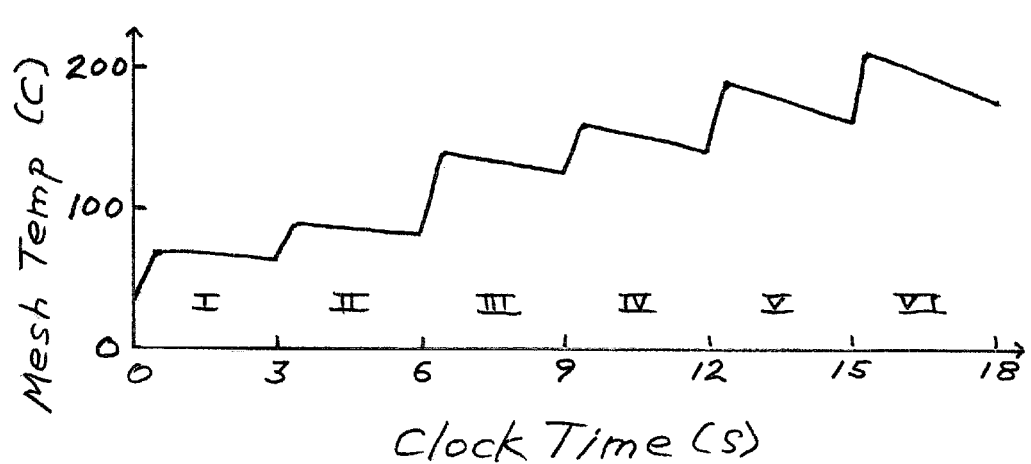

FIG. 7 shows an example of a battery-powered supply 18 combined with an analog IPHC circuit 44 that controls the length of the heating period. At the beginning of a heating period, (t=0), timer 56 is externally triggered and then provides a control signal 43 that closes MOSFET power switch 42. Battery 40 (e.g., 12 V) drives a high current, I, through mesh 12, thereby resistively heating it. Voltage taps on both sides of mesh 12, $V_a$, $V_b$, are provided to multiplier 50 in real-time. Multiplier 50 determines the voltage drop, $V_b-V_a$, across mesh 12, and then squares this value to get $(V_b-V_a)^2$. Integrator 52 then integrates the output of multiplier 50, $(V_b-V_a)^2$, over time to produce an output that is proportional to the total amount of energy deposited in the mesh by resistive heating. The delta temperature rise in the mesh is proportional to total energy deposited, if the energy lost due to thermal radiation is not too great. Comparator 54 continuously compares the output voltage from integrator 52 (which represents the deposited energy) to a set point (i.e., reference) voltage. When the output of integrator 52 exceeds the reference voltage, then comparator 54 tells timer 56 to open switch 42 and stop the resistive heating. If the battery's voltage is low, then it will take longer for the time-integral of the voltage drop across the mesh to reach the desired reference value. In this way, IPHC 44 adjusts the length of time that the current flows through the mesh in order to compensate for changes in the battery's voltage. A simple variable resistor or potentiometer can be used in IPHC 44 to adjust the set point reference voltage of comparator 54. Trial and error can be used to determine what specific reference voltage is needed to attain a desired temperature rise, for a given type of mesh (e.g., pleated or flat), mesh holder, etc. Timer 56 can also perform a safety function that will open power switch 42 and interrupt heating if the heating time has gone longer than, e.g., 1-2 seconds. This is to prevent accidental damage to the mesh due to overheating.

For a multi-step heating profile, the set point reference values (which can be different for each of the multiple steps) can be provided to IPHC 44 by a PC or microprocessor 48 via D/A board 46. Table 2 shows examples of sets of comparator reference voltages for a six-step temperature profile, for a flat mesh (swipe sample) and a pleated mesh (vapor sample), respectively. The stepped profiles in Table 2 achieve a peak mesh temperature of about 200 C The voltages needed for heating the pleated mesh are about 2-3 times greater than for the flat mesh, because the pleated mesh has more thermal mass then the flat mesh. Typically, the dwell time in-between heating pulses is about 3 seconds, and the typical heating period is about 0.3 seconds. Both the dwell time and the heating time period can vary from step to step within a multiple-step desorption cycle. The specific reference voltages in Table 2 were determined by trial and error, using an IR sensor to measure the actual mesh temperatures during desorption cycles with a Sandia Micro-Hound™ portable IMS platform. This table of reference voltages, along with the trigger voltage timing schedule (i.e., triggered every 3 seconds), is programmed into PC 48, and supplied to IPHC 44 via D/A board 46 (which can also perform A/D conversion for providing data to PC 48).

TABLE 2

Examples of Comparator Reference Voltages for a 6-step Profile, giving a peak temperature of about 200 C.

| Comparator Reference Voltage (V) | Pleated Mesh (vapor) | Flat Mesh (swipe) |
| --- | --- | --- |
| Step 1 | 0.30 | 0.12 |
| Step 2 | 0.37 | 0.15 |
| Step 3 | 0.27 | 0.13 |
| Step 4 | 0.40 | 0.15 |
| Step 5 | 0.47 | 0.17 |
| Step 6 | 0.42 | 0.15 |

FIGS. 8A-D show examples of profiles of (A) Reference Voltage, (B) Trigger Voltage, (C) Mesh Current, and (D) Mesh Temperature, as a function of clock time for a 6-step desorption cycle and a pleated mesh. The dwell time is about 2.7-3.0 seconds in this example. The reference voltages are the same as listed in Table 2 for the pleated mesh. The reference voltage changes (if need be) every 3 seconds, i.e., at the start of each new step. The trigger voltage (e.g., +5 V), is applied for the first 2 seconds of each 3 second step, and then reset to zero for the remaining 1 second of each step. The mesh current, I, is applied for roughly 0.3 seconds at the beginning of each of the six steps. The amount of current (e.g., 20 amps), is determined primarily by the battery's voltage and the mesh's resistance, however, the period of time that the current flows (i.e., the heating time period) is variable and can be controlled by IPHC 44 as described above. Nominally this heating period is about 0.3 seconds, but this period varies in accordance with the specific reference voltage assigned to each of the six steps, as well as any changes in battery voltage that may occur during the six steps. The total desorption heating cycle takes about 18 seconds, in this example. The mesh temperature starts at about 30 C, and rises to a peak of about 200 C at the beginning of the last step (i.e., step 6). The temperature is relatively flat during the dwell periods for the first two steps. However, the amount of temperature drop that occurs during the dwell period becomes progressively more pronounced as the mesh temperature increases stepwise throughout the remaining steps 3-6, primarily due to radiation heat loss (which increases with increasing temperature raised to the fourth power).

Optionally, power supply 18 may comprise a feedback-controlled closed-loop system, wherein the actual mesh temperature is measured in real-time (e.g., by using an IR sensor) and fed-back to power supply 18, which continuously adjusts the mesh current in real-time to drive the measured temperature towards the desired temperatures. Alternatively, PC 48 may be used as the feedback-controlled closed-loop system, in conjunction with power supply 18.

In one embodiment, the invention comprises a method for controllably releasing contaminants from a contaminated porous metallic mesh during a thermal desorption cycle, the method comprising the following steps:

a) providing a contaminated porous metallic mesh in gaseous communication with a chemical detector;

b) increasing the temperature of the mesh in a series of at least two stepped temperature rises, by sequentially performing at least two consecutive heating steps, wherein each heating step comprises:

1) applying a heating pulse by resistively heating the mesh for a heating time period by passing an electric current directly through the mesh from one edge of the mesh to an opposite edge of the mesh, thereby generating Joule-type electrical resistance heating directly in the mesh;

2) increasing the temperature of the mesh during the heating pulse and thermally desorbing a batch of contaminant molecules; followed by 3) not heating the mesh for a dwell time period that is at least 2 times longer than the heating time period; and c) carrying the batch of contaminant molecules to the chemical detector for subsequent detection and analysis.

Certain embodiments of the invention may comprise the steps of using an Integrating Preconcentrator Heat Controller to compensate for any drop in the battery's voltage by integrating the resistive heating power over time during a heating pulse, and then adjusting the length of the heating time period so that a consistent amount of heat energy is delivered to the mesh, thereby causing a consistent temperature rise in the mesh, despite changes in the battery's voltage. Additionally, the steps may further comprise measuring the voltage drop across the mesh when electricity is flowing, squaring the voltage drop, integrating the square of the voltage drop over time, comparing the value of the integral to a reference setpoint value, and then deciding whether or not to stop the heating pulse by opening a switch and stopping the flow of electricity to the mesh when the value of the integral exceeds the reference setpoint value; wherein the reference setpoint value is a predetermined voltage that is proportional to a desired amount of heat energy to be generated in the mesh.

Other embodiments of the present invention comprise a system for controllably releasing contaminants from a contaminated porous metallic mesh during a thermal desorption cycle, the system comprising:

a contaminated porous metallic mesh in gaseous communication with a chemical detector;

resistance heating means for increasing the temperature of the mesh in a series of at least two stepped temperature rises, by sequentially performing at least two consecutive heating steps, wherein each heating step comprises:

1) applying a heating pulse by resistively heating the mesh for a heating time period by passing an electric current directly through the mesh from one edge of the mesh to an opposite edge of the mesh, thereby generating Joule-type electrical resistance heating directly in the mesh;

2) increasing the temperature of the mesh during the heating pulse and thermally desorbing a batch of contaminant molecules; followed by 3) not heating the mesh for a dwell time period that is at least 2 times longer than the heating time period; and means for carrying the batch of contaminant molecules to the chemical detector for subsequent detection and analysis.

Additional descriptions of the use of porous metallic preconcentrator meshes for in trace detection systems can be found in U.S. Pat. No. 5,854,431 to Linker et al.; U.S. Pat. No. 5,915,268 to Linker et al.; U.S. Pat. No. 6,085,601 to Linker et al. (now reissued as RE38797); U.S. Pat. No. 6,523,393 to Linker et al.; U.S. Pat. No. 6,334,365 to Linker and Brusseau; U.S. Pat. No. 6,345,545 to Linker and Brusseau; U.S. Pat. No. 6,572,825 to Linker and Hannum; U.S. Pat. No. 6,604,406 to Linker et al.; and U.S. Pat. No. 6,848,325 to Parmeter et al.; all of which are incorporated herein by reference.

The particular examples discussed above are cited to illustrate particular embodiments of the invention. Other applications and embodiments of the apparatus and method of the present invention will become evident to those skilled in the art. It is to be understood that the invention is not limited in its application to the details of construction, materials used, and the arrangements of components set forth in the following description or illustrated in the drawings.

The scope of the invention is defined by the claims appended hereto.

What is claimed is:

1. A method for controllably releasing contaminants from a contaminated porous metallic mesh during a thermal desorption cycle, comprising:

a) providing a contaminated porous metallic mesh in gaseous communication with a chemical detector;

b) increasing the temperature of the mesh in a series of at least two stepped temperature rises, by sequentially performing at least two consecutive heating steps, wherein each heating step comprises:

1) applying a heating pulse by resistively heating the mesh for a heating time period by passing an electric current directly through the mesh from one edge of the mesh to an opposite edge of the mesh, thereby generating Joule-type electrical resistance heating directly in the mesh;

2) increasing the temperature of the mesh during the heating pulse and thermally desorbing a batch of contaminant molecules; followed by 3) not heating the mesh for a dwell time period that is at least 2 times longer than the heating time period; and c) carrying the batch of contaminant molecules to the chemical detector for subsequent detection and analysis.

2. The method of claim 1, wherein the maximum temperature of the mesh does not exceed 220 C in any heating pulse.

3. The method of claim 1, wherein the length of the heating time period is variable and can vary from one heating step to another.

4. The method of claim 1, wherein the mesh is made of a metal alloy selected from the group consisting of stainless steel, Ferralloy, Hastalloy, an Inconel alloy, Inconel 601, Inconel 625, and Inconel 718; wherein the mesh is not coated with an organic or polymeric material.

5. The method of claim 1, wherein the total number of consecutive heating steps in the desorption cycle is 2-7 steps.

6. The method of claim 1, wherein the porous metallic mesh is contaminated with one or more explosive compounds selected from the group of consisting of TNT, RDX, PETN, and HMX.

7. The method of claim 1, wherein the porous metallic mesh is securely held by a mesh holder comprising:
- a pair of electrically-insulated, opposed panels pivotally connected to each other along one edge by a hinge, with panel latching means for clamping and tightly holding the mesh between the panels, the mesh being electrically insulated from the panels; and
- a pair of spaced electrical contacts mounted on the panels such that when the mesh is clamped and tightly held by the holder, the contacts touch the mesh and make good electrical contact.

8. The method of claim 1, wherein the reactive ion population comprises methylene chloride.

9. The method of claim 1, further comprising measuring the mesh temperature in real-time, and providing the measured temperature in real-time to a closed-loop feedback control means for controlling the amount of current resistively heating the mesh in such a way that the measured temperature history more closely follows a desired temperature history.

10. The method of claim 1, wherein the chemical detector comprises one or more detectors selected from the group consisting of ion mobility spectrometer (IMS), mass spectrometer (MS), surface acoustic wave sensor (SAW), electron capture device (ECD), differential mobility spectrometer (DMS), chemiluminescence detectors (CLD), gas chromatograph (GC), and thermo redox detector; and miniaturized versions of these, including MEMS versions of these.

11. The method of claim 1, wherein the mesh is made of stainless steel, and is coated with an organic or polymeric material.

12. The method of claim 1, wherein the chemical detector comprises an Ion Mobility Spectrometer (IMS), having an initial population of reactive ions.

13. The method of claim 12, wherein the length of the dwell time period between each consecutive heating period is sufficiently long so that at least 80% of the initial population of reactive ions in the IMS is recovered prior to applying another heating pulse.

14. The method of claim 12, wherein carrying the batch of contaminant molecules to the chemical detector in each heating step comprises flowing clean and dry air through or across the mesh.

15. The method of claim 1, wherein the heating time period is less than or equal to about 0.5 seconds, and the dwell time period is about 1-10 seconds.

16. The method of claim 15, wherein the length of the dwell time period is 2-4 seconds.

17. The method of claim 16, wherein:
- the desorption cycle comprises 6 consecutive heating steps;
- the length of the dwell time period is about 3 seconds;
- the length of the heating time period is about 0.3 seconds
- the peak mesh temperature during the first heating step is about 70-75 C;
- the peak mesh temperature during the second heating step is about 90-95 C;
- the peak mesh temperature during the third heating step is about 140-145 C;
- the peak mesh temperature during the fourth heating step is about 160-165 C;
- the peak mesh temperature during the fifth heating step is about 195-200 C; and
- the peak mesh temperature during the sixth heating step is about 205-210 C.

18. The method of claim 1, further comprising using a battery to provide the voltage needed to drive the electric current to resistively heat the mesh during a heating pulse.

19. The method of claim 18, further comprising using an Integrating Preconcentrator Heat Controller to compensate for any drop in the battery's voltage by integrating the resistive heating power over time during a heating pulse, and then adjusting the length of the heating time period so that a consistent amount of heat energy is delivered to the mesh, thereby causing a consistent temperature rise in the mesh, despite changes in the battery's voltage.

20. The method of claim 19, further comprising measuring the voltage drop across the mesh when electricity is flowing, squaring the voltage drop, integrating the square of the voltage drop over time, comparing the value of the integral to a reference setpoint value, and then deciding whether or not to stop the heating pulse by opening a switch and stopping the flow of electricity to the mesh when the value of the integral exceeds the reference setpoint value; wherein the reference setpoint value is a predetermined voltage that is proportional to a desired amount of heat energy to be generated in the mesh.

21. A method for controllably releasing contaminants from a contaminated porous metallic preconcentrator mesh during a desorption cycle, comprising:
a) providing a contaminated porous metallic preconcentrator mesh in gaseous communication with an Ion Mobility Spectrometer (IMS); the IMS having an initial population of reactive ions; and
b) increasing the temperature of the mesh in a series of at least two stepped temperature rises by sequentially performing at least two consecutive heating steps, wherein each heating step comprises:
1) applying a heating pulse by resistively heating the mesh for a heating time period by passing an electric current directly through the mesh from one edge of the mesh to an opposite edge of the mesh, thereby generating Joule-type electrical resistance heating directly in the mesh;
2) increasing the temperature of the mesh during the heating pulse and thermally desorbing a batch of contaminant molecules; followed by
3) not heating the mesh for a dwell time period that is at least 2 times longer than the heating time period; and
c) carrying the batch of contaminant molecules to the IMS for subsequent detection and analysis;
wherein the heating time period is less than or equal to about 0.5 seconds, and the dwell time period is about 1-10 seconds;
wherein the maximum temperature of the mesh does not exceed 220 C in any heating pulse;
wherein the length of the heating time period is variable and can vary from one heating step to another; and
wherein the length of the dwell time period between each consecutive heating period is sufficiently long so that at least 80% of the initial population of reactive ions in the IMS is recovered prior to applying another heating pulse.

22. A system for controllably releasing contaminants from a contaminated porous metallic mesh during a thermal desorption cycle, comprising:

a contaminated porous metallic mesh in gaseous communication with a chemical detector;

resistance heating means for increasing the temperature of the mesh in a series of at least two stepped temperature rises, by sequentially performing at least two consecutive heating steps, wherein each heating step comprises:

1) applying a heating pulse by resistively heating the mesh for a heating time period by passing an electric current directly through the mesh from one edge of the mesh to an opposite edge of the mesh, thereby generating Joule-type electrical resistance heating directly in the mesh;

2) increasing the temperature of the mesh during the heating pulse and thermally desorbing a batch of contaminant molecules; followed by 3) not heating the mesh for a dwell time period that is at least 2 times longer than the heating time period; and means for carrying the batch of contaminant molecules to the chemical detector for subsequent detection and analysis.

23. The system of claim 22, wherein the porous metallic mesh comprises a porous metallic preconcentrator mesh.

24. The system of claim 22, wherein the mesh is made of a metal alloy selected from the group consisting of stainless steel, Ferralloy, Hastalloy, an Inconel alloy, Inconel 601, Inconel 625, and Inconel 718; wherein the mesh is not coated with an organic or polymeric material.

25. The system of claim 22, wherein the means for carrying the batch of contaminant molecules to the Ion Mobility Spectrometer in each heating step comprises a fan disposed to flow and dry air through or across the mesh.

26. The system of claim 22, further comprising a mesh holder for securely holding the porous metallic mesh inside of the thermal desorption chamber, the holder comprising:

a pair of electrically-insulated, opposed panels pivotally connected to each other along one edge by a hinge, with panel latching means for clamping and tightly holding the mesh between the panels, the mesh being electrically insulated from the panels; and a pair of spaced electrical contacts mounted on the panels such that when the mesh is clamped and tightly held by the holder, the contacts touch the mesh and make good electrical contact.

27. The system of claim 22, wherein the reactive ion gas comprises methylene chloride.

28. The system of claim 22, further comprising means for measuring the mesh temperature in real-time and providing the measured temperature in real-time to a closed-loop feedback control means for controlling the amount of current resistively heating the mesh in such a way that the measured temperature history more closely follows a desired temperature history.

29. The system of claim 22, wherein the chemical detector comprises one or more detectors selected from the group consisting of ion mobility spectrometer (IMS), mass spectrometer (MS), surface acoustic wave sensor (SAW), electron capture device (ECD), differential mobility spectrometer (DMS), chemiluminescence detectors (CLD), gas chromatograph (GC), and thermo redox detector; and miniaturized versions of these, including MEMS versions of these.

30. The system of claim 22, wherein the porous metallic mesh comprises one or more porous structures selected from the group consisting of a metallic filter, a felt or felt-like mat of finely-drawn wires, a woven screen of metal wires, a porous foamed metal structure, a microporous metallic filter with microholes, and a felt-like mat of sintered metal wires.

31. The system of claim 22, wherein the mesh is made of stainless steel, and is coated with an organic or polymeric material.

32. The system of claim 31, wherein the organic or polymeric material is selected from the group consisting of nano-carbon; carbon nanotubes, a carbon molecular sieve adsorbent resin, a porous polymer resin based on 2,6-diphenylene-oxide, cyclo-dextrin, beta-cyclodextrin, beta-cyclodextrin hydrate, hydroxypropyl-beta-cyclodextrin, hydroxyethyl-beta-cyclodextrin, methyl-beta-cyclodextrin, cycloheptaamylose, glucose-beta-cyclodextrin, a quaternary ammonium salt, benzalkonium chloride, benzethonium chloride, cetylpyridinium chloride, myristalkonium chloride, benzyl (C12-C16) alkydimethylammonium chloride, cetalkonium chloride, cetyl trimethyl ammonium chloride, dodecyl trimethyl ammonium chloride, stearyl trimethyl ammonium chloride, alkyl dimethyl ammonium salt, cetyl tetra ammonium bromide, cetyl trimethyl ammonium bromide (CTAB), a CTAB sol-gel, cetyl ethyl dimethyl ammonium bromide, tetradecyl trimethyl ammonium bromide, tetrabutyl ammonium bromide, cyanopropyl phenyl methyl silicone, and combinations thereof.

33. The system of claim 22, wherein the resistance heating means comprises a DC battery for providing the voltage needed to drive the electric current to resistively heat the mesh during a heating pulse.

34. The system of claim 33, further comprising an Integrating Preconcentrator Heat Controller circuit means for compensating for any drop in the battery's voltage by integrating the power generated in the mesh over time during a heating pulse, and then adjusting the length of the heating time period so that a consistent amount of heat energy is delivered to the mesh, thereby causing a consistent temperature rise in the mesh, despite changes in the battery's voltage.

35. The system of claim 34, wherein the Integrating Preconcentrator Heat Controller circuit means comprises means for measuring the voltage drop across the mesh when electricity is flowing, squaring the voltage drop, integrating the square of the voltage drop over time, comparing the value of the integral to a reference setpoint value, and then deciding whether or not to stop the heating pulse by opening a switch and stopping the flow of electricity to the mesh when the value of the integral exceeds the reference setpoint value; wherein the reference setpoint value is a pre-determined voltage that is proportional to a desired amount of heat energy to be generated in the mesh.

36. A system for controllably releasing contaminants from a contaminated porous metallic preconcentrator mesh during a desorption cycle, comprising:

a contaminated porous metallic preconcentrator mesh in gaseous communication with an Ion Mobility Spectrometer (IMS); the IMS having an initial population of reactive ions; and resistance heating means for increasing the temperature of the mesh in a series of at least two stepped temperature rises by sequentially performing at least two consecutive heating steps, wherein each heating step comprises:

1) applying a heating pulse by resistively heating the mesh for a heating time period by passing an electric current directly through the mesh from one edge of the mesh to an opposite edge of the mesh, thereby generating Joule-type electrical resistance heating directly in the mesh;
2) increasing the temperature of the mesh during the heating pulse and thermally desorbing a batch of contaminant molecules; followed by
3) not heating the mesh for a dwell time period that is at least 2 times longer than the heating time period; and means for carrying the batch of contaminant molecules to the IMS for subsequent detection and analysis;

wherein the heating time period is less than or equal to about 0.5 seconds, and the dwell time period is about 1-10 seconds;

wherein the maximum temperature of the mesh does not exceed 220 C in any heating pulse;

wherein the length of the heating time period is variable and can vary from one heating step to another; and wherein the length of the dwell time period between each consecutive heating period is sufficiently long so that at least 80% of the initial population of reactive ions in the IMS is recovered prior to applying another heating pulse.

* * * * *